United States Patent [19]

Yock

[11] Patent Number: 5,451,207
[45] Date of Patent: Sep. 19, 1995

[54] METHOD OF CORONARY PLAQUE REMOVAL WITH BYPASS AND PERFUSION

[75] Inventor: Paul G. Yock, Hillsborough, Calif.

[73] Assignee: The Regents of the University of California, Oakland, Calif.

[21] Appl. No.: 232,921

[22] Filed: Apr. 25, 1994

[51] Int. Cl.6 .............................................. A61M 31/00
[52] U.S. Cl. .......................................... 604/53; 604/4
[58] Field of Search ........................................ 604/4–8, 604/22, 50–54; 600/16–18

[56] References Cited

U.S. PATENT DOCUMENTS

| | | |
|---|---|---|
| 3,513,845 | 5/1970 | Chesnut et al. ........................... 604/4 |
| 4,456,000 | 6/1984 | Schjeldahl et al. . |
| 4,459,977 | 7/1984 | Pizon et al. . |
| 4,661,094 | 4/1987 | Simpson . |
| 4,771,777 | 9/1988 | Horzewski et al. . |
| 4,804,365 | 2/1989 | Litzie et al. . |
| 4,898,575 | 2/1990 | Fischell et al. . |
| 4,994,027 | 2/1991 | Farrell . |
| 4,994,033 | 2/1991 | Shockey et al. . |
| 5,000,185 | 3/1991 | Yock . |
| 5,011,469 | 4/1991 | Buckberg et al. . |
| 5,100,424 | 3/1992 | Jang et al. . |
| 5,117,831 | 6/1992 | Jang et al. . |
| 5,135,484 | 8/1992 | Wright . |
| 5,163,905 | 11/1992 | Michael . |
| 5,195,942 | 3/1993 | Weil et al. . |
| 5,248,297 | 9/1993 | Takase . |
| 5,383,854 | 1/1995 | Safar et al. ............................ 604/98 |

Primary Examiner—Corrine Maglione
Attorney, Agent, or Firm—Townsend and Townsend Khourie and Crew

[57] ABSTRACT

Catheter-based coronary surgery is performed in a system which includes a combination of bypass of the heart, perfusion of the heart and the use of a therapeutic catheter to loosen plaque deposited in a coronary artery. Bypass is done with a bypass circuit circulating blood from the right atrium through an extracorporeal bypass unit and back through a femoral artery. Perfusion is done by passing a perfusate into the heart for retrograde flow, then drawing the perfusate out of the heart through a catheter which also serves as a guide for the therapeutic catheter. The open distal end of the guide is placed sufficiently close to the functional element at the end of the therapeutic catheter that plaque which has been loosened by the action of the therapeutic catheter is carried into the guide along with the perfusate, and hence out of the patient's body.

12 Claims, 3 Drawing Sheets

METHOD OF CORONARY PLAQUE REMOVAL WITH BYPASS AND PERFUSION

BACKGROUND OF THE INVENTION

Medical research directed to the removal or abatement of coronary stenoses and other vascular obstructions has generated a variety of therapies and surgical and nonsurgical procedures, as well as sophisticated equipment both to perform and to monitor these procedures. A procedure of increasing popularity is percutaneous transluminal angioplasty since it does not involve thoracotomy. Consequently, angioplasty poses a lesser risk of postoperative complications such as postpericardotomy syndrome, hepatitis, and stroke, plus a lesser risk of mortality, while allowing a faster recovery of the patient. In addition, recent surveys have shown that the effectiveness of angioplasty compares well with that of surgical techniques, in terms of the abatement of coronary obstructions as well as the incidence of the reoccurrence of such obstructions.

Angioplasty techniques have their limitations, however, and these are particularly pronounced in situations where the coronary restriction is severe. In conditions where the plaque which causes the obstruction spans the cross section of the vessel entirely, it may not be possible to penetrate and span the obstructed region with the angioplasty balloon. Also, since angioplasty merely compresses the plaque against the vessel wall rather than removing it, the procedure may be of limited effect, or susceptible to an early reoccurrence of the obstruction. To address these concerns, catheters and catheter systems have been developed which loosen and remove the plaque from the vessel rather than merely compressing it. Loosening is achieved by a variety of ablation techniques, such as cutting, abrasion, emulsification and the use of ultrasound or lasers, while removal is achieved through lumens in the catheter shafts. Even with techniques such as these, however, it is not possible to remove all plaque from the obstructed vessel, and plaque which has been loosened but not removed creates a risk of acute problems subsequent to the procedure, recurrence of the blockage condition, or both. A further problem encountered in both angioplasty and plaque loosening and removal techniques is that these procedures are performed while the heart is still beating. The movement caused by the beating heart makes it difficult to determine the precise location of the plaque and to effect its complete removal.

SUMMARY OF THE INVENTION

These and other problems associated with catheter-based methods of coronary surgery are addressed by the present invention, which resides in a non-surgical method of plaque detachment and removal performed in conjunction with non-surgical bypass and heart muscle perfusion.

In accordance with this invention, bypass of the heart is achieved by a bypass circuit which draws blood from the fight atrium by way of a catheter which extends into the atrium, and returns the blood to the arterial system, preferably by way of a catheter which enters the femoral artery and may extend upward into the iliac artery or the descending aorta. Perfusion is performed on the muscle of the left side of the heart in the retrograde direction, and is achieved in any of various ways. In one method, the perfusate is a solution from an external source, such as an enhanced saline solution, and is introduced into the coronary sinus by way of a catheter and directed through the left side of the heart in the retrograde direction. In another method, the patient's blood is used as the perfusate, the blood being drawn from the aorta through a catheter, then passed through a perfusion circuit external to the patient's body for oxygen enrichment, and returned to the coronary sinus from which it passes into the heart tissue in the same manner as the enhanced saline solution in the preferred method. A third method is a hybrid of these two methods, in which the patient's blood is drawn and oxygenated as in the second method above, then diluted with enhanced saline solution before being returned to the coronary sinus.

Plaque detachment and removal are achieved by a therapeutic, or debulking, catheter which extends through the heart and into the coronary arteries. A guide catheter extending into the aorta serves as a passageway for the insertion of the therapeutic catheter. The functional portion of the therapeutic catheter is a cutting, abrading, or otherwise plaque-loosening or ablating mechanism at or close to the distal end of the therapeutic catheter. The therapeutic catheter is advanced through the guide catheter and positioned by conventional means so that this functional portion lies in the region of vascular disease. With a vacuum applied to it, the guide catheter also serves as a conduit for the removal of the perfusate passing through the heart muscle after being introduced at the coronary sinus. The distal opening of the guide catheter is therefore positioned proximal to the functional element of the therapeutic catheter, preferably in the ostium of the artery being treated, so that debris from the debulking action of the therapeutic catheter is carried along with the perfusate as the perfusate enters the guide.

In further preferred embodiments of the invention, the guide catheter which serves as the passageway for the therapeutic catheter is the inner guide catheter of a pair of concentric guide catheters, the outer catheter of the pair (i.e., the outer guide) extending less far distally than the inner guide and the annular space between the two providing a further passageway which can serve a variety of functions. One such function is to serve as a further means of removing loosened plaque debris. To achieve this, a light and gentle vacuum is imposed in the annular space, and any debris which fails to enter the inner guide along with the perfusate will then enter the annular space. In other functions, the annular space may serve as a conduit for additional catheters to either introduce or withdraw fluids or other materials from the heart. For example, the additional catheter may be used to provide a supplemental perfusion of the heart muscle. One such supplemental perfusion is anterograde perfusion of the right side of the heart, achieved by directing and anchoring the additional catheter into the appropriate ostium. This can be done concurrently with the retrograde perfusion of the left side performed with the aid of the inner guide. In another example, the additional catheter may terminate inside the aortic root and be used to introduce flushing saline for a more extensive flushing of the aortic root subsequent to the action of the therapeutic catheter.

Stoppage of the heart during the procedure by way of the bypass circuit permits plaque removal to be performed in a manner which is quick, accurate, and complete. The capture and removal of debris liberated from the arterial wall by the perfusate (whether using an externally supplied solution or blood drawn from the heart as the perfusate) lessens the risk of postoperative complications such as stroke.

The present invention permits the use of catheters delivered through the femoral vessels for manipulation of all components and the performance of all procedures involved in the implementation of the invention. Accordingly, thoracotomy is not part of the procedure; instead, the only required incisions are cut-downs in the femoral area. By eliminating thoracotomy, the procedure offers a significantly reduced convalescence time and subjects the heart and lungs to considerably less trauma. It is further expected that the rate of recurrence of the condition will be less, and postoperative longevity of the patient greater, with this procedure than with either bypass surgery or angioplasty or other catheter techniques. Unlike surgery, the procedure of this invention uses the native vessels as the conduits for bypass, perfusion and plaque removal, and unlike angioplasty or the atherectomy techniques as they are currently known, this procedure removes the large majority, if not all, of the plaque deposit.

These and other features, objects, and advantages of the invention will be apparent from the description which follows.

DETAILED DESCRIPTION OF THE INVENTION AND PREFERRED EMBODIMENTS

Figure 1:
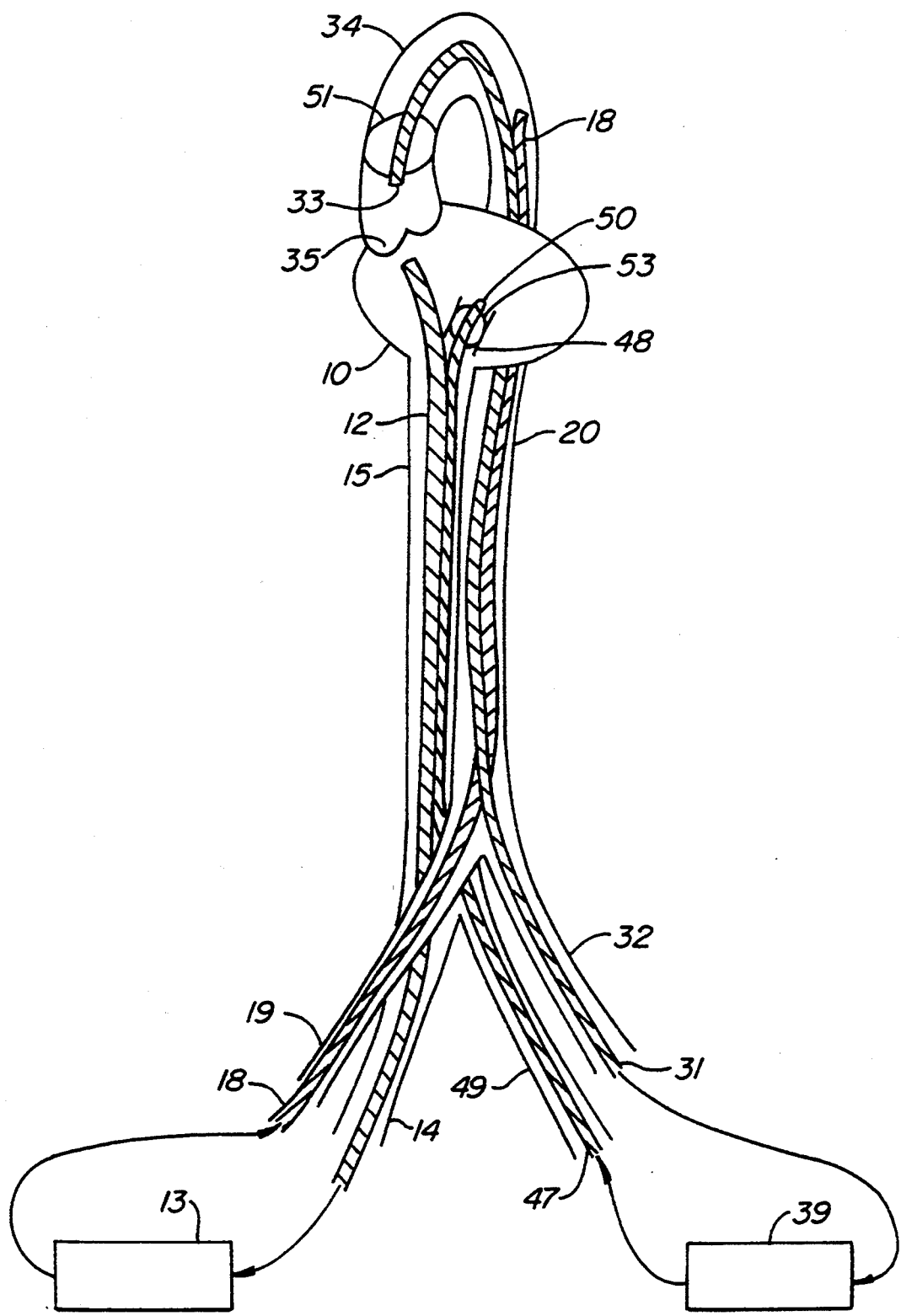
FIG. 1 is a representation, partially in the form of a block diagram, of the primary vascular conduits through which the various catheters in one implementation of the present invention are introduced. The bypass and perfusion circuits are shown.

This description is made with reference to a particular embodiment or means of implementation of the invention, as shown in the drawings. This embodiment is used for purposes of illustrating the underlying concepts which are central to all embodiments of the invention, as will be clear from the description.

Figure 2:
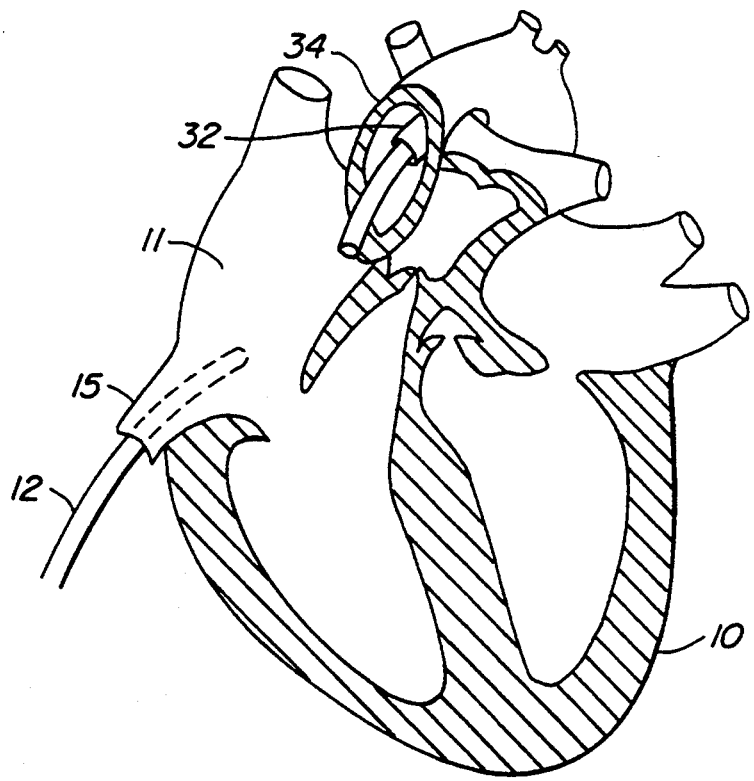
FIG. 2 is a drawing of the human heart, in partial cross section, showing the chambers of the heart and vessels adjacent to the heart where the catheters are introduced.

FIG. 1 depicts elements of an overall system, showing how the various circuits and components operate in conjunction with one another. FIG. 2 is a cross section of the heart, showing the distal tips of the catheters and their location. FIGS. 1 and 2, examined together, illustrate that the heart 10 is bypassed by drawing blood from the right atrium 11 into a catheter 12. Blood from this catheter is then passed through a bypass circuit 13 external to the patient's body, where the blood is pumped, oxygenated, and otherwise treated prior to being returned to the patient. The catheter 12 drawing blood from the patient may be positioned in the heart by any conventional catheterization route. A convenient method, and one in accordance with prevailing catheterization techniques, involves introduction of the catheter by way of a femoral vein 14, from which the catheter is guided by conventional steering and monitoring techniques up through the vena cava 15 into the fight atrium 11.

Blood leaving the external bypass circuit is returned to the patient through a second catheter 18 which is likewise conveniently introduced by way of a femoral artery 19. In this particular embodiment, the returning catheter 18 extends into the descending aorta as shown in FIG. 1. The femoral vein 14 and femoral artery 19 selected for the two catheters 12, 18 of the bypass system are most conveniently selected as those on the same side of the patient (i.e., both on the left side or both on the right), although opposite sides may also be used.

The extracorporeal portion 13 of the bypass circuit can be conventional in its composition, including the selection and arrangement of its components. Typical components included in known systems of this type are one or more pumps, which may be either displacement pumps, centrifugal pumps or both, an oxygenator to enrich the oxygen content of the blood, and a filter to remove particulate matter or debris from the blood. Additional components such as bubble detectors and reservoirs may also be included, as well as monitoring devices to monitor such parameters as pressure and temperature, and control circuits to make appropriate adjustments to one or more pumps and heating units in response to the monitors.

Perfusion, as indicated above, is performed by introducing perfusate into the coronary sinus so that the perfusate will pass in the retrograde direction through the left side of the heart, then drawing the perfusate out through the guide catheter which also serves as a passageway for the therapeutic catheter. This retrograde perfusion is illustrated in FIG. 1. A catheter 47 introduces the perfusate into the vasculature with the distal end of the catheter inside the coronary sinus 48. Most conveniently, the catheter 47 enters the vasculature at the femoral vein 49 on the same side of the patient as the femoral artery 32 through which the inner and outer guide catheters have been inserted. Perfusate is supplied to this catheter at a positive pressure of approximately 10 to 100 mm of mercury, to force the perfusion blood to flow in the retrograde direction. The guide catheter through which the perfusate leaves the patient's body at the end of its passage through the heart muscle may be a single-lumen catheter or the inner catheter of a pair of concentric catheters. If a single-lumen catheter is used, the catheter will preferably extend directly into the ostium of the artery being treated, and will preferably contain an occlusion balloon surrounding its distal end to seal off the ostium and thereby assure that all perfusate enters the catheter lumen. As an alternative to the occlusion balloon, sealing of the ostium can be achieved by the use of a catheter with a flared soft tip which is larger than the ostium of the artery. With a suction applied to the catheter, its tip will engage the ostium by suction force. If a concentric catheter pair is used, the outer catheter will preferably terminate in the ascending aorta, with a surrounding occlusion balloon to seal off the aorta, while the inner catheter will extend into the ostium without the need for its own occlusion balloon. A more detailed discussion of the occlusion balloons is presented below.

In preferred embodiments, a concentric pair of guide catheters is used. The drawings illustrate such an embodiment. Like the catheters of the bypass circuit, the outer guide catheter 31 is introduced into the vasculature by any conventional catheterization route. Most conveniently, the outer guide catheter 31 enters the body at the femoral artery 32 on the opposite side of that used for the bypass circuit. Thus inserted, the outer guide catheter 31 is advanced until its distal end 33 is inside the ascending aorta 34, preferably the ascending aorta, and most preferably in close proximity to the aortic root 35.

Figure 3:
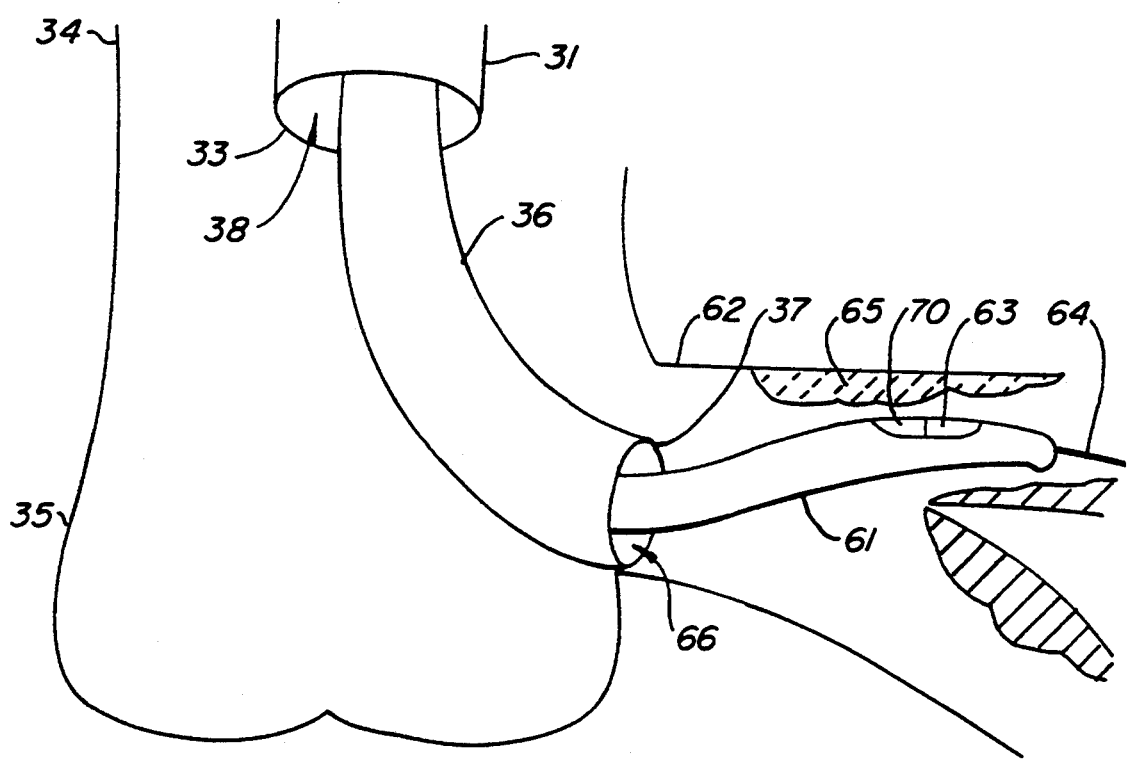
FIG. 3 is an enlargement of the aortic root, showing the distal ends of the inner and outer guide catheters and the therapeutic and imaging catheter in use on a plaque deposit.

An enlarged view of the interior of the aorta 34 and the distal open ends of the inner and outer guide catheters is shown in FIG. 3. The inner guide catheter 36 is passed through the lumen of the outer guide catheter 31, with the distal end 37 of the inner guide catheter extending beyond the opening at the distal end 33 of the outer guide catheter. The annular space 38 between the outer and inner guide catheters therefore commences at the distal end 33 of the outer guide catheter, which as indicated above is in the ascending aorta 34.

Like the extracorporeal portion 13 of the bypass circuit, the extracorporeal elements 39 used to prepare the perfusate can be conventional in their selection and arrangement. These elements are shown as a perfusion circuit in FIG. 1, similar to the extracorporeal bypass circuit. Typical perfusion systems include one or more pumps, an oxygenator, a filter, and a cooling element to lower the temperature of the perfusate for purposes of slowing down the metabolic rate of the heart. Additional components such as bubble detectors, reservoirs, pressure and temperature monitors and the like may also be included. While the two extracorporeal systems 13 and 39 are shown as separated systems in FIG. 1, they may also be integrated into a single system, particularly in applications where a perfusate is used which consists of the patient's own blood oxygenated and diluted with enhanced saline. The arrangement of an integrated system will be known to those skilled in this art.

While the left side of the heart is being perfused in retrograde manner, perfusion of the right side of the heart can also be performed, either retrograde in the manner described above, or by selective anterograde perfusion. The arrangement shown in FIG. 4 can be used for the anterograde perfusion. In this arrangement, a perfusate introduction catheter 41 is passed through the outer guide catheter 31, which is large enough to accommodate both the perfusate introduction catheter 41 and the inner guide catheter 36. The perfusate introduction catheter 41 is directed into the right coronary artery 42.

In preferred embodiments of the invention, the passageways around the exteriors of some of the catheters are closed by toroidal occlusion balloons. These balloons serve to anchor the catheters in position and control the direction of fluid flow around the catheter. These balloons are located in close proximity to the distal ends of the catheters, and when inflated, these balloons span the gap between the outer surface of the catheter and the inner surface of the vessel in which the catheter is positioned.

For example, the outer guide catheter 31 in the embodiment shown in the drawings has an occlusion balloon 51 surrounding the full circumference of its exterior surface near its distal opening 33. Thus positioned, the balloon 51 anchors the catheter to the aorta 20, and closes the aorta to permit flow to occur only through the lumens of the outer and inner guide catheters. This balloon 51 permits a pressure differential to be maintained between the portion of the aorta distal to the balloon and the portion proximal to the balloon. Thus, as perfusate which has escaped the inner guide catheter 36 is drawn into the annular passage 38 between the outer and inner guide catheters, the pressure on the distal side of the balloon is less than the systemic pressure on the proximal side, and only the perfusate is drawn into the annular passage.

Figure 4:
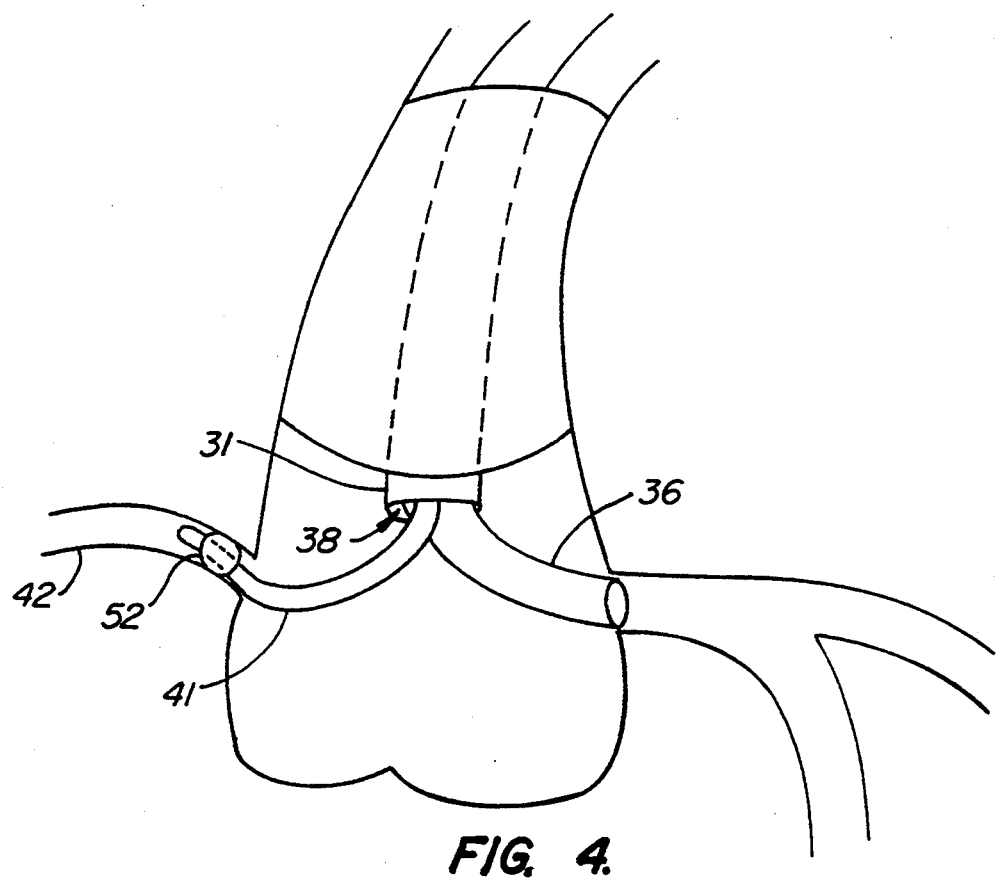
FIG. 4 is a view similar to that of FIG. 3, showing catheters arranged for anterograde perfusion.

Likewise, the perfusion catheter 41 shown in FIG. 4 for anterograde perfusion of the right side of the heart has an occlusion balloon 52 surrounding its full circumference near its distal end. This anchors the catheter in place and assures flow of the perfusate in the anterograde direction, rather than bypassing the desired flow path through the coronary artery and passing directly into the annular space 38 inside the outer guide catheter 31. As seen in FIG. 1, the catheter 47 supplying the perfusate for retrograde perfusion likewise has an occlusion balloon 53 surrounding its full circumference near its distal end. This assures that the perfusion blood entering the system will flow in the retrograde direction, and that the elevated pressure at the entry point will be retained.

Returning to FIG. 3, the inner guide catheter 36 serves as a guide for the therapeutic catheter 61, and terminates at a point either inside or close to the ostium of the coronary artery 62 in which the stenosis is found. Coronary guide catheters designed specifically for left coronary arteries and those designed specifically for right coronary arteries are currently in wide use, differentiated from each other by the shape and direction of curvature of these catheters at their distal ends. These guide catheters, or optionally ones which are substantially the same except for the inclusion of a mechanism or structural element as described above for sealing the catheter to the vessel, or for different materials of construction, can be used effectively in this application. When it is necessary to perform the procedure on blockages in coronaries on both the left and tight sides, an atherectomy procedure in accordance with the present invention may use a left coronary guide catheter and a fight coronary guide catheter in succession. One is readily exchanged for the other without removal of the outer guide catheter.

The therapeutic catheter 61 can be one which employs any of the variety of plaque detachment techniques currently known, all remotely controlled from the proximal end. Examples of these techniques are mechanical cutting or abrading techniques, techniques involving the injection of a dissolving or emulsifying liquid or an abrading slurry, and techniques involving the use of ultrasound or laser beams. Preferred techniques are those which loosen the plaque and reduce it to particulate matter.

The functional element 63 of the therapeutic catheter, i.e., the cutting, abrading or pulverizing element which acts directly on the deposited plaque, is placed in the region of the deposited plaque. This is accomplished by inserting and manipulating the catheter by conventional means. The location of the stenosis can be identified, for example, by an angiogram performed by the use of x-rays and an appropriate dye. The therapeutic catheter can also be positioned in a similar manner. Typical means of achieving this involve the use of a therapeutic catheter, a guidewire, or both, with an imaging element at the tip. A variety of imaging technologies are known to those skilled in the art of catheter design, and may be used here. Radiopaque markers, for example, are widely used. Another example is ultrasonic imaging, which can be achieved by the placement of an ultrasonic transducer at the catheter tip. Fluoroscopic imaging is another example, and can be achieved by the placement of a contrast medium through the diseased artery. Other possibilities will be readily apparent to those skilled in the art. Disclosures of some of these technologies can be found in U.S. Pat. No. 5,000,185 to Yock, P. G. issued Mar. 19, 1991; U.S. Pat. No. 5,100,424 to Jang, Y. T., et al., Mar. 31, 1992; and U.S. Pat. No. 5,117,831 to Jang, Y.-T., et al., Jun. 2, 1992. In the embodiment shown in FIG. 3, the imaging element 70 is positioned at the tip of the therapeutic catheter adjacent to the therapeutic element.

The therapeutic catheter is generally positioned by first directing a guidewire 64 through and beyond the inner guide catheter 36 to the coronary artery which contains the stenosis. The guidewire 64 can be of conventional construction, and will generally contain a flexible, slightly curved tip (not shown) to aid in the steering of the guidewire into the desired artery. Once the tip of the guidewire has penetrated and passed the stenosis, the therapeutic catheter 61 is inserted over the guidewire, using a lumen through the therapeutic catheter as a conduit for the guidewire.

With the therapeutic catheter 61 positioned such that its functional dement 63 at the stenosis, introduction of perfusate solution into the coronary sinus is begun and a suction is imposed on the interior of the inner guide catheter 36. The functional dement 63 of the therapeutic catheter is then activated. The opening 37 of the inner guide catheter is sufficiently close to the functional element 63 of the therapeutic catheter that loosened particulate plaque is drawn into the annular space 66 between the two catheters with minimal loss of the plaque due to dispersion away from the entrance of the inner guide catheter, or due to the plaque becoming caught in some other vascular passage, or the plaque escaping into the vasculature. The perfusate entering the annular space 66 can then either be discarded or treated to remove the debris and return the perfusate to the patient's body.

As mentioned above, loose plaque flowing past the opening 37 of the inner guide catheter and thereby escaping entry into the annular space 66 between the inner guide and therapeutic catheters can be made to pass into the distal opening 33 of the outer guide catheter 31 and through the annular space 38 between the outer and inner guide catheters by applying a gentle suction to the outer guide catheter.

Figure 5:
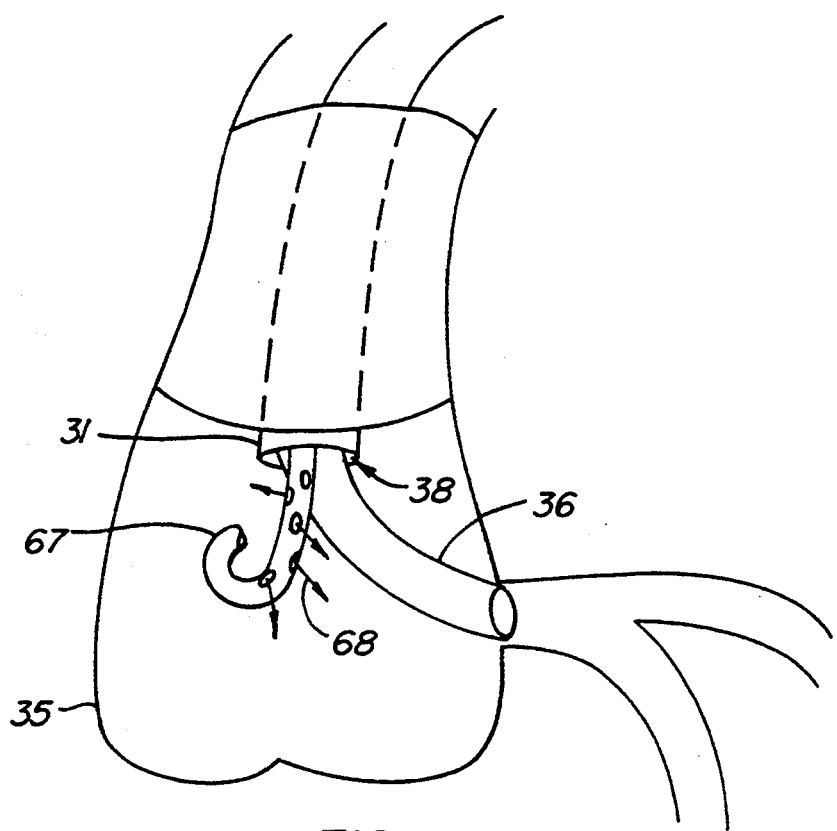
FIG. 5 is a view similar to that of FIGS. 3 and 4, showing catheters arranged for flushing of the aortic root following the clearing of the stenosis.

Further removal of debris which may have collected in the aortic root may be achieved by the inserting of a flushing catheter into the root, as shown in FIG. 5. The flushing catheter 67 is introduced into the aortic root 35 through the lumen of the outer guide catheter 31. A flushing fluid 68 such as physiological saline is introduced through this catheter, while a gentle suction is maintained in the annular space 38 between it and the outer guide catheter, thereby fluidizing the debris and drawing it out.

The following is a description of one example of a procedure which employs the concepts of this invention, showing a sequence of steps and functions to implement the various circuits described above.

For purposes of consistency, the bypass circuit in this example is joined to the patient's vasculature through the femoral artery 19 and vein 14 on the patient's right side, and the perfusion circuit is joined to the patient's vasculature through the femoral artery 32 and vein 49 on the left side. The procedure is begun with a femoral cutdown, in which the bypass return catheter or cannula 18 is inserted into the right femoral artery 19 up to the descending aorta, and the bypass removal catheter 12 is inserted into the right femoral vein 14 and directed to the fight atrium 11. The large guide catheter 31 (referred to above as the "outer guide catheter") is then inserted into the patient's left femoral artery 32. A pacer is preferably inserted as well, and this can be done through the left femoral vein 49. A coronary sinus perfusion catheter 47 is inserted in the left femoral vein 49 as well, and directed into the coronary sinus for retrograde perfusion.

Bypass connections are then made, joining the bypass removal 12 and return 18 catheters to the extracorporeal bypass circuit 13, and bypass is begun. Perfusion of the heart is then begun by feeding perfusate solution into the coronary sinus through the coronary sinus perfusion catheter 47. The occlusion balloon 51 encircling the large guide catheter 31 near its distal end 33 is inflated to block blood flow into the aorta 34, and a low suction is applied to the catheter. The occlusion balloon 53 encircling the coronary sinus perfusion catheter 47 is also inflated to direct the perfusion blood to flow in the retrograde direction.

An appropriately selected coronary guide catheter 36 (referred to above as the "inner guide catheter") is then inserted through the large guide catheter 31 and directed to the coronary where the treatment is needed. Dye is then injected and x-rays taken to obtain an angiogram, the heart having been stopped by the bypass circuit.

A guidewire 64 is then inserted through the coronary guide 36 into the first branch 62 of the coronary arteries, and through the region of the stenosis. The therapeutic catheter 61 is then inserted over the guidewire 64. Once the therapeutic catheter is in place, a low suction is applied to the coronary guide 36, and the functional element 63 at the tip of the therapeutic catheter is activated. The plaque deposits 65 are thus loosened and drawn into the coronary guide 36 where they are removed from the body.

Once the stenosis is cleared, the guidewire 64 and therapeutic catheter 61 may be partially withdrawn for repositioning inside a different branch of the coronary arteries on the same side, and the procedure repeated. In addition, the guidewire 64, therapeutic catheter 61 and coronary guide 36 may all be withdrawn entirely and the coronary guide replaced with an oppositely directed coronary guide, i.e., a right coronary guide may be exchanged for a left one, or vice versa. The guidewire 64 and therapeutic catheter 61 are then reintroduced, this time however extending into the coronary arteries on the opposite side, which are then treated in the same manner as those of the first side.

At the completion of the plaque removal, a second angiogram with the heart stopped is taken. The aortic root 68 is then flushed thoroughly by the perfusion circuit. The occlusion balloon 51 encircling the large guide catheter is then deflated, and perfusion of the coronaries is begun. The bypass is then terminated and normal blood flow is resumed.

All components of the system used in the method described above are fabricated of conventional materials. The outer and inner guide catheters and the coronary sinus perfusion catheter may, for example, be of silicone rubber, polyvinyl chloride, polyethylene terephthalate or the like. The guidewire and therapeutic catheter are typically of stainless steel and similar materials.

Likewise, conditions of operation are similar to or compatible with those used in heart catheterization procedures of the prior art. For example, the flow rate for the bypass circuit can range from about 2.0 to about 5.0 liters per minute, while the flow rate for the perfusion circuit can range from about 50 to about 400 milliliters per minute. Conventional methods of performing angiograms, and otherwise monitoring the procedure with conventional monitoring, imaging and recording equipment, can be used.

The foregoing is offered primarily for purposes of illustration. It will be readily apparent to those skilled in the art that the operating conditions, materials, procedural steps and other parameters of the system described herein may be further modified or substituted in various ways without departing from the spirit and scope of the invention.

What is claimed is:

1. A method for removing plaque from a blood vessel adjacent to a patient's heart, said method comprising:
   (a) bypassing said heart by drawing blood from a right atrium of said heart, passing blood so drawn through an extracorporeal bypass circuit at a controlled rate, and returning blood from said extracorporeal bypass circuit to a first femoral artery of said patient;
   (b) liberating plaque deposited in said blood vessel with a plaque debulking catheter extending coaxially through a guide catheter extending into said heart; and
   (c) perfusing said heart in a retrograde direction by passing perfusate through said heart to said blood vessel and drawing said perfusate from said blood vessel into said guide catheter, thereby drawing liberated plaque into said guide catheter with said perfusate.

2. A method in accordance with claim 1 in which said guide catheter is defined as an inner guide catheter, and said inner guide catheter extends coaxially through an outer guide catheter of sufficient diameter to leave an annular passage between said inner and outer guide catheters, said inner and outer guide catheters having open distal ends, and steps (b) and (c) are performed with the open distal end of said inner guide catheter extending further distally than the open distal end of said outer guide catheter.

3. A method in accordance with claim 2 in which steps (b) and (c) are performed with said open distal end of said inner guide catheter positioned inside said blood vessel and said open distal end of said outer guide catheter positioned inside the ascending aorta.

4. A method in accordance with claim 3 further comprising drawing liberated plaque not drawn into said inner guide catheter into said annular passage between said inner and outer guide catheters.

5. A method in accordance with claim 2 in which steps (b) and (c) further comprise stopping blood flow over the exterior of said outer guide catheter by a toroidal occlusion balloon affixed to said outer guide catheter.

6. A method in accordance with claim 1 in which step (c) comprises introducing said perfusate (perfusion blood) into a coronary sinus associated with said heart.

7. A method in accordance with claim 2 in which step (c) further comprises stopping blood flow over the exterior of said outer guide catheter by a first toroidal occlusion balloon affixed to said outer guide catheter, introducing said perfusate into a coronary sinus associated with said heart through a coronary sinus catheter, and stopping blood flow over the exterior of said coronary sinus catheter by a second toroidal occlusion balloon affixed to said coronary sinus catheter.

8. A method in accordance with claim 1 in which step (a) comprises:
   (i) drawing blood from said right atrium into a bypass catheter inserted into said patient through a first femoral vein and terminating in said fight atrium;
   (ii) passing blood so drawn through said extracorporeal bypass circuit at a controlled rate; and
   (iii) returning blood from said extracorporeal bypass circuit to said first femoral artery.

9. A method in accordance with claim 2 in which step (a) comprises:
   (a)(i) inserting into a first femoral vein of said patient a bypass catheter to place the distal end thereof in said fight atrium;
   (a)(ii) inserting into said first femoral artery a cannula;
   (a)(iii) drawing blood from said fight atrium into said distal end of said bypass catheter and through said extracorporeal bypass circuit, and returning blood from said extracorporeal bypass circuit to said cannula; and step (c) comprises:
   (c)(i) inserting into a second femoral artery of said patient said outer guide catheter with said inner guide catheter passing therethrough coaxially, the distal end of said outer guide catheter extending into an ascending portion of said aorta;
   (c)(ii) inserting into a second femoral vein of said patient a perfusion catheter, the distal end thereof extending into a coronary sinus of said heart; and
   (c)(iii) passing perfusate into said coronary sinus through said perfusion catheter and drawing said perfusate from said heart through said inner guide catheter.

10. A method in accordance with claim 1 in which step (b) comprises:
    (b)(i) passing a guidewire through said guide catheter, into a blood vessel having a region bearing an excessive plaque deposit, and across said region;
    (b)(ii) advancing a plaque debulking catheter along said guidewire to a position where a debulking device on said plaque debulking catheter is in contact with said excessive plaque deposit; and
    (b)(iii) and operating said debulking device to loosen plaque from said deposit.

11. A method in accordance with claim 10 in which said debulking device is one employing a member selected from the group consisting of cutting, abrading, emulsification and laser ablation.

12. A method in accordance with claim 10 in which said plaque debulking catheter includes an imaging element, and step (b)(ii) further comprises guiding said plaque debulking catheter to said position with the aid of said imaging element.

* * * * *

UNITED STATES PATENT AND TRADEMARK OFFICE
CERTIFICATE OF CORRECTION

PATENT NO. : 5,451,207
DATED : September 19, 1995
INVENTOR(S) : Paul G. Yock

It is certified that error appears in the above-indentified patent and that said Letters Patent is hereby corrected as shown below:

In Column 1, line 60, change "fight" to --right--.
In Column 4, line 5, change "fight" to --right--.
In Column 6, line 43, change "fight" to --right--.
In Column 7, lines 28 and 31, change "dement" to --element--.
In Column 10, lines 17, 26, and 28, change "fight" to --right--.

Signed and Sealed this

Sixteenth Day of January, 1996

Attest:

BRUCE LEHMAN

*Attesting Officer*  *Commissioner of Patents and Trademarks*